US00PP22732P2

(12) United States Plant Patent
Kuijf

(10) Patent No.: US PP22,732 P2
(45) Date of Patent: May 15, 2012

(54) ***POTENTILLA* PLANT NAMED 'KUPINPA'**

(50) Latin Name: *Potentilla fruticosa*
Varietal Denomination: Kupinpa

(76) Inventor: Hendricus Jacobus Maria Kuijf, Amstelhoek (NL)

( * ) Notice: Subject to any disclaimer, the term of this patent is extended or adjusted under 35 U.S.C. 154(b) by 2 days.

(21) Appl. No.: 12/927,271

(22) Filed: Nov. 10, 2010

(51) Int. Cl.
*A01H 5/00* (2006.01)

(52) U.S. Cl. ..... Plt./237

(58) Field of Classification Search ..... Plt./237
See application file for complete search history.

*Primary Examiner* — Susan McCormick Ewoldt
(74) *Attorney, Agent, or Firm* — Jondle & Associates, P.C.

(57) ABSTRACT

A new *Potentilla* plant particularly distinguished by its deep pink colored semi-double flowers and narrow upright and compact growth habit, is disclosed.

2 Drawing Sheets

Genus and species: *Potentilla fruticosa.*
Variety denomination: 'Kupinpa'.

BACKGROUND OF THE NEW PLANT

The present invention comprises a new and distinct variety of *Potentilla* plant, botanically known as *Potentilla fruticosa* and hereinafter referred to by the variety name 'Kupinpa'. 'Kupinpa' is the result of a naturally occurring whole-plant mutation in the summer of 2006, in the nursery of the Applicant, in Amstelhoek, the Netherlands, of the parent plant 'Pink Beauty' (U.S. Plant Pat. No. 9,874). A single plant selection was subsequently chosen for further evaluation and asexual propagation.

'Kupinpa' was first propagated via softwood cuttings in the summer of 2006 and has been asexually reproduced by softwood cuttings in Amstelhoek, the Netherlands for over four generations. 'Kupinpa' has been found to retain its distinctive characteristics through successive asexual propagations via softwood cuttings.

Plant Breeder's Rights for this variety were applied for in Europe on Nov. 4, 2009. 'Kupinpa' has not been sold or made publicly available more than one year prior to the filing date of this application.

SUMMARY OF THE INVENTION

The following are the most outstanding and distinguishing characteristics of this new variety when grown under normal horticultural practices in Amstelhoek, Netherlands.

1. Eye-catching deep pink flowers; and
2. Semi-double flowers.

DESCRIPTION OF THE PHOTOGRAPHS

This new *Potentilla* plant is illustrated by the accompanying photographs which show overall plant habit including blooms, buds, and foliage of the plant; the colors shown are as true as can be reasonably obtained by conventional photographic procedures.

DESCRIPTION OF THE NEW VARIETY

Figure 1:
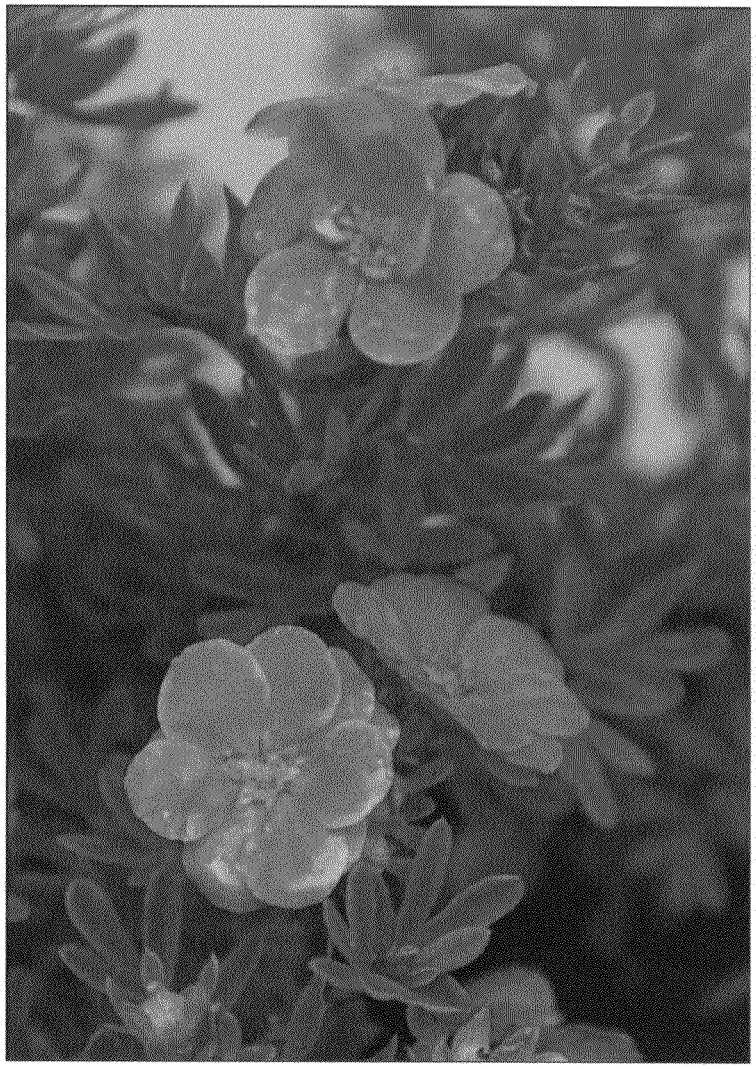
FIG. 1 depicts a close-up view of the flowers.
Figure 2:
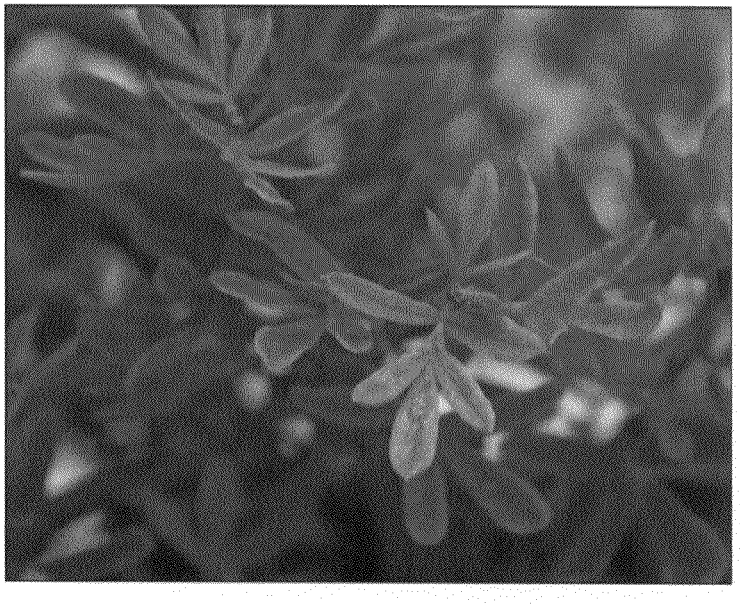
FIG. 2 depicts a close-up view of the foliage.
Figure 3:
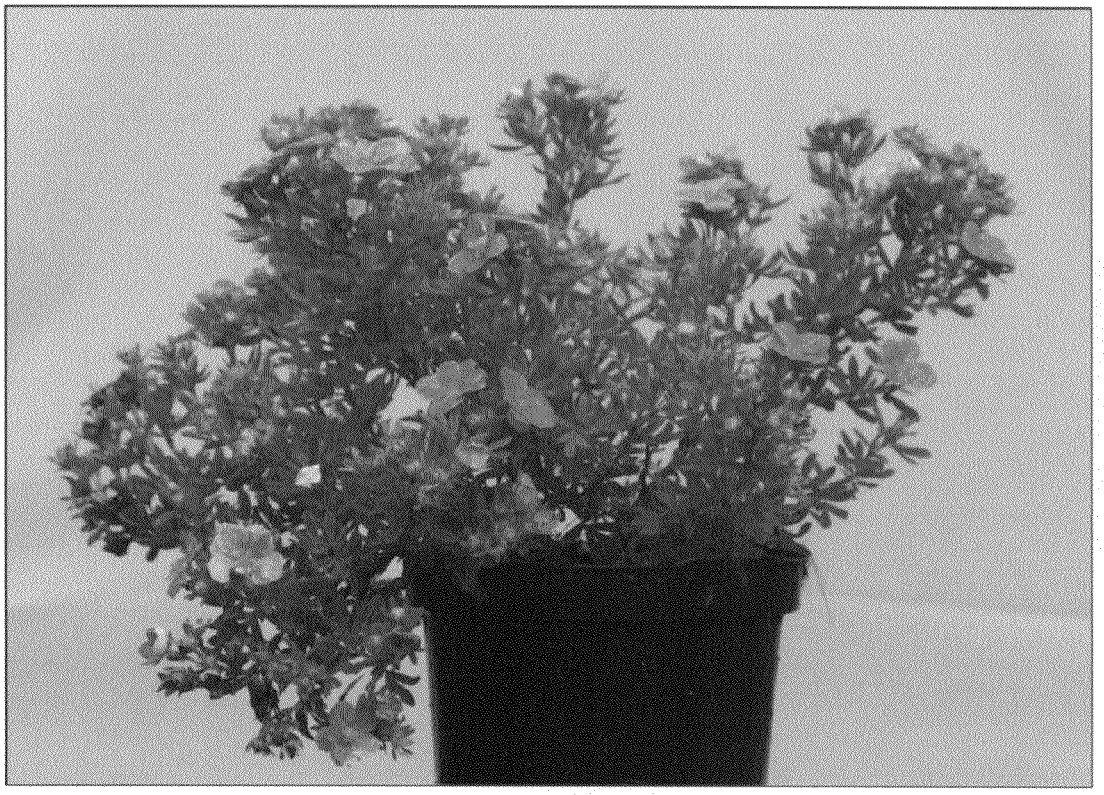
FIG. 3 depicts the overall plant habit including blooms, buds, and foliage.

The following detailed description sets forth the distinctive characteristics of 'Kupinpa'. The data which define these characteristics were collected from asexual reproductions carried out in Amstelhoek, the Netherlands. The plant history was taken in September of 2010 on 2 year old plants grown outdoors in 2 liter containers. Color readings were taken under natural light. Color references are primarily to The R.H.S. Colour Chart of The Royal Horticultural Society of London (R.H.S.) ($5^{th}$ edition 2007).

DETAILED BOTANICAL DESCRIPTION OF THE NEW PLANT

Classification:
- *Family.*—Rosaceae.
- *Botanical.*—*Potentilla fruticosa.*
- *Common.*—Cinquefoil.

Type: Perennial deciduous shrub.

Growth:
- *Time to flower.*—Approximately 15 months after cuttings are made.
- *Growth rate.*—Approximately 8.0 cm per season (young plants grow faster).

Plant:
- *Shape.*—Globular.
- *Growth habit.*—Broad upright.
- *Vigor.*—Moderate.
- *Height.*—21.3 cm.
- *Diameter.*—35.1 cm.
- *Branching.*—Habit: Moderately free branching. Basal branching: Present. Number of lateral branches per plant: 34. Lateral branch length: 11.3 cm. Lateral branch diameter: 0.2 cm. Internode length: 1.5 cm.

Stems:
- *Shape.*—Rounded.
- *Appearance.*—Dull.
- *Texture.*—Rough to the touch due to short stiff hairs.
- *Aspect.*—Rounded.
- *Strength.*—Very strong.

*Color*.—Young stems: Between RHS 145B and RHS 145C (Yellow-green). Bark: Between RHS 186C and RHS 186D (Greyed-purple). Older stems: RHS 174A (Greyed-orange). Bark: RHS 174A (Greyed-orange).

*Pubescence*.—Present. Length of hairs: 0.1 cm. Color: RHS 157D (Green-white).

Foliage:

*Leaf arrangement*.—Alternate.

*Compound or single*.—Compound.

*Quantity of leaves per lateral branch*.—8. Quantity of leaflets per leaf: 3.

*Color*.—Immature foliage: Upper surface: Between RHS 144A and RHS 144B (Yellow-green). Lower surface: RHS 145A (Yellow-green). Mature foliage: Upper surface: RHS 143A (Green) to RHS 146B (Yellow-green). Lower surface: RHS 138B (Green).

*Leaf*.—Division: Trifoliate. Shape: Broad ovate. Length: 2.2 cm. Width: 2.4 cm. Venation pattern: Palmate. Vein color (of both leaf and leaflet): Upper surface: Between RHS 143A (Green) and RHS 146B (Yellow-green). Lower surface: Between RHS 138C and RHS 138D (Green). Petiole: General: Sessile. Length: 0.8 cm. Diameter: 0.07 cm. Color: RHS 145A (Yellow-green). Stipule: Present on each side of the base of the petiole. Shape: Ovate. Length: 0.6 cm. Width: 0.2 cm. Color (both surfaces): Between RHS 199B and RHS 199C (Grey-brown). Pubescence: Upper surface: Very sparsely pubescent. Length of hairs: 0.1 cm. Color: RHS 157D (Green-white). Lower surface: Sparsely pubescent. Margins: Sparsely pubescent.

*Leaflet*.—Division: Trifoliate; overall appearance is palmate with 5 leaflets. Shape: Obovate to elliptic. Length: 1.6 cm. Top (trifoliate) leaflet: 1.9 cm. Width: 0.5 cm. Top (trifoliate) leaflet: 1.5 cm. Venation pattern: Pinnate. Vein color (of both leaf and leaflet): Upper surface: Between RHS 143A and RHS 146B. Lower surface: Between RHS 138C and RHS 138D.

*Leaf and leaflet apex*.—Short apiculate.

*Leaf and leaflet base*.—Attenuate.

*Leaf and leaflet texture*.—Slightly glossy, sparsely pubescent.

*Margin of leaf and leaflet*.—Entire.

Flower bud:

*Length*.—0.8 cm.

*Diameter*.—0.6 cm.

*Shape*.—Broad ovate.

*Color*.—RHS 150B (Yellow-green) and RHS 150A at the tip (Darker yellow-green).

*Rate of opening*.—Approximately 5 days.

Flowers:

*Arrangement*.—Terminal placed flowers, solitary or in pairs.

*Type*.—Semi-double, rotate.

*Flowering habit*.—Once a year from early June to mid-October.

*Quantity*.—Flowers per lateral stem: Average of 3. Flower buds per lateral stem: Average of 11. Flowers and buds per plant: Average of 475.

*Fragrance*.—Absent.

*Aspect*.—Upright to slightly outward.

*Shape*.—Rotate.

*Diameter*.—2.9 cm.

*Depth*.—0.7 cm.

*Longevity of flower on plant*.—Average of 5 days.

*Petal*.—Quantity per flower: Average of 10. Appearance: Smooth, dull. Texture (both surfaces): Smooth, glabrous. Arrangement: Rotate. Shape: Orbicular to broad obovate. Apex: Obtuse. Base: Unfused. Margin: Entire. Length: 1.4 cm. Width: 1.3 cm. Color: Upper surface when opening: RHS 61C (Red-purple). Lower surface when opening: Between RHS 158C and RHS 158D (Yellow-white) with margins of RHS 182D (Greyed-red). Upper surface when fully opened: RHS N57D (Red-purple). Lower surface when fully opened: Between RHS 158C and RHS 158D (Yellow-white) with margins of RHS 182D (Greyed-red). Overall petal color fades to: RHS 58D (Red-purple).

*Petaloids*.—Absent.

*Sepal*.—Quantity per flower: Average of 10. Appearance: Smooth, dull. Arrangement: Rotate. Shape: 5 are ovate and 5 are narrow oblong. Apex: Acute. Base: Ovate sepals: Broad cuneate. Narrow oblong sepals: Narrow cuneate. Margin: Entire. Length (both shapes): 0.8 cm. Width: Ovate sepals: 0.4 cm. Narrow oblong sepals: 0.25 cm. Color: Immature upper surface: Ovate sepals: RHS 150B (Yellow-green) with RHS 151B (Darker yellow-green) tips. Narrow oblong sepals: RHS 143A (Green). Immature lower surface: Ovate sepals: RHS 150B (Yellow-green) with RHS 151B (Darker yellow-green) tips. Narrow oblong sepals: RHS 143B (Green). Mature upper surface: Ovate sepals: RHS 150B (Yellow-green) with RHS 151B (Darker yellow-green) tips. Narrow oblong sepals: RHS 143A (Green). Mature lower surface: Ovate sepals: RHS 150B (Yellow-green) with RHS 151B (Darker yellow-green) tips. Narrow oblong sepals: RHS 143B (Green).

*Calyx*.—Shape: Rotate and flat. Length: 0.3 cm. Diameter: 2.2 cm.

*Peduncle*.—Absent.

*Pedicels*.—Length: 1.0 cm. Diameter: 0.1 cm. Angle: Average of 20° (0° equals straight on top of lateral branch). Strength: Moderately strong. Color: Between RHS 145B and RHS 145C (Yellow-green).

Reproductive organs:

*Stamen quantity*.—Average of 25.

*Anther*.—Shape: Ovate and flattened. Size: Length: Average of 0.1 cm. Width: Average of 0.05 cm. Color: RHS 22A.

*Filament length*.—Average of 0.2 cm.

*Pollen quantity*.—Low.

*Pollen color*.—RHS 14A (Yellow-orange).

*Pistil quantity*.—Average of 30.

*Pistil length*.—0.2 cm.

*Stigma shape*.—Sessile and diffuse.

*Stigma color*.—Between RHS 153B and RHS 153C (Yellow-green).

*Style length*.—0.1 cm.

*Style color*.—Between RHS 153B and RHS 153C (Yellow-green).

*Ovary color*.—Between RHS 144B and RHS 144C (Yellow-green), with short soft hairs. Average length of hairs: 0.05 cm. Color: RHS 157D (Green-white).

Fruit and seed set: No fruit or seed have been observed.

Disease and insect/pest resistance: Good, similar to other *Potentilla fruticosa* plants.

High temperature tolerance: Tolerant up to 40° C.
Low temperature tolerance: Tolerant to USDA Zone 3.

COMPARISON WITH PARENT AND COMMERCIAL VARIETIES

'Kupinpa' differs from the parent plant 'Pink Beauty' (U.S. Plant Pat. No. 9,874) by having a narrow, upright, and compact growth habit, while 'Pink Beauty' has a broad, upright, and semi-compact growth habit. Additionally, 'Kupinpa' has deep pink semi-double flowers, while 'Pink Beauty' has light pink single flowers.

'Kupinpa' differs from 'UMan' (U.S. Plant Pat. No. 12,258) by having deep pink semi-double flowers, while 'UMan' has single bi-colored flowers which are a deep yellow with an orange-red color radiated outward from the center.

I claim:

1. A new and distinct variety of *Potentilla fruticosa* plant named 'Kupinpa' as described and shown herein.

* * * * *